United States Patent
Bulgarelli et al.

(10) Patent No.: US 11,382,845 B2
(45) Date of Patent: Jul. 12, 2022

(54) ORGANIC COMPOUNDS

(71) Applicant: GIVAUDAN SA, Vernier (CH)

(72) Inventors: Nelly Bulgarelli, Loveland, OH (US); Ian Michael Harrison, Poissy (FR); Emmanuel Aussant, Paris (FR)

(73) Assignee: GIVAUDAN SA, Vernier (CH)

( * ) Notice: Subject to any disclaimer, the term of this patent is extended or adjusted under 35 U.S.C. 154(b) by 0 days.

(21) Appl. No.: 16/638,897

(22) PCT Filed: Sep. 25, 2018

(86) PCT No.: PCT/EP2018/075885
§ 371 (c)(1),
(2) Date: Feb. 13, 2020

(87) PCT Pub. No.: WO2019/063515
PCT Pub. Date: Apr. 4, 2019

(65) Prior Publication Data
US 2020/0360243 A1  Nov. 19, 2020

(30) Foreign Application Priority Data
Sep. 26, 2017 (GB) .................................. 1715535.9

(51) Int. Cl.
| | | |
|---|---|---|
| *A61K 8/11* | (2006.01) | |
| *A61K 8/73* | (2006.01) | |
| *A61K 8/88* | (2006.01) | |
| *A61Q 19/10* | (2006.01) | |
| *A61Q 5/12* | (2006.01) | |
| *A61Q 5/02* | (2006.01) | |
| *A61Q 15/00* | (2006.01) | |

(52) U.S. Cl.
CPC ................ *A61K 8/11* (2013.01); *A61K 8/736* (2013.01); *A61K 8/88* (2013.01); *A61Q 5/02* (2013.01); *A61Q 5/12* (2013.01); *A61Q 15/00* (2013.01); *A61Q 19/10* (2013.01)

(58) Field of Classification Search
CPC .. A01N 25/28; A61K 8/736; A61K 2800/412; A61K 8/84; A61K 8/88; A61K 8/11; A61Q 15/00; A61Q 19/00; A61Q 19/10; A61Q 5/02; A61Q 5/12; B01J 13/14; C11D 3/505
See application file for complete search history.

(56) References Cited

U.S. PATENT DOCUMENTS

| | | | |
|---|---|---|---|
| 4,138,362 A | | 2/1979 | Vassiliades et al. |
| 2013/0330292 A1* | | 12/2013 | Lei ........................... B01J 13/14 424/70.17 |
| 2015/0252312 A1* | | 9/2015 | de Villeneuve ......... A23L 27/72 510/515 |

FOREIGN PATENT DOCUMENTS

| | | |
|---|---|---|
| WO | 2014130204 A1 | 8/2014 |
| WO | 2016144798 A1 | 9/2016 |

OTHER PUBLICATIONS

GB Search Report for corresponding application GB1715535.9 dated Feb. 13, 2018.
International Search Report and Written Opinion of the International Searching Authority for corresponding application PCT/EP2018/075885 dated Jan. 29, 2019.

\* cited by examiner

*Primary Examiner* — Anna R Falkowitz
(74) *Attorney, Agent, or Firm* — Norris McLaughlin PA

(57) ABSTRACT

Core-shell microcapsules comprising a hydrophobic core surrounded by a shell comprising a thermosetting resin comprising moieties derived from polyisocyanates, substantially unprotonated chitosan and another amine different from chitosan, characterized in that the substantially unprotonated chitosan is delivered in the solid, powder form to the locus of the encapsulation reaction. The core-shell microcapsules are provided in the form of a slurry comprising 10 to 50 wt % of microcapsules, based on the total weight of the slurry, and the shell of the microcapsules comprises from 0.1 to 20 wt % of moieties derived from chitosan, based on the total weight of the shell.

19 Claims, No Drawings

ORGANIC COMPOUNDS

This is an application filed under 35 USC 371 based on PCT/EP2018/075885, filed 25 Sep. 2018, which in turn is based on GB 1715535.9 filed 26 Sep. 2017. The present application claims the full priority benefit of these prior applications and herein incorporates by reference the full disclosures of these prior applications.

FIELD

The present invention relates to composition comprising polyurea-based core-shell microcapsules, derived from polyisocyanates and chitosan, in a suspending medium, to methods of forming said microcapsules, and to applications of these microcapsules in consumer products.

BACKGROUND OF THE INVENTION

It is known to incorporate encapsulated functional ingredients in consumer products, such as household care, personal care, and fabric care products. The functional ingredients are encapsulated for a variety of reasons. Microcapsules can isolate and protect the functional ingredients from external suspending media, such as consumer product bases, in which they may be incompatible or unstable. They are also used to assist in the deposition of functional ingredients onto substrates, such as skin, hair, fabrics or a variety of household surfaces.

Microcapsules can also act as means of controlling the spatio-temporal release of functional ingredients, such as perfumes, essential oils, pesticides, pheromones and cosmetic ingredients.

Encapsulating perfume ingredients, and particularly low molecular weight and volatile perfume ingredients may, however, be challenging because in many instances, these ingredients tend to leak out from the microcapsules with time. This is especially the case of microcapsules dispersed in product bases containing high level of extracting solvents of surfactants. These solvents and surfactants include, for example, non-ionic surfactants, especially those having ethylene oxide moieties, and solvents, such as short chain alcohols, short chain glycols and glycol ethers, glycerol and the like. Such solvents and surfactants often can be found in fabric care detergents, cleansing compositions and shampoos. The leakage is a kinetic effect, which occurs during storage and accelerates as the temperature is increased. Typical storage tests involve submitting microcapsule-containing products to prolonged storage, for example one month or more, under elevated temperature conditions, for example 40° C. or more. Under such conditions, part or whole of the encapsulated material may leak out of the microcapsules. Furthermore, in cases in which a perfume composition is encapsulated, selective leakage of perfume ingredients may occur, leading to undesired distortion or denaturation of the perfume olfactive note. As a consequence, the microcapsules become less effective in providing the controlled release effect that they were designed to provide.

Accordingly, many attempts have been made to decrease the permeability of microcapsule shells. In this respect, aminoplast thermosetting resins are known to be particularly suitable for encapsulating perfume compositions. Such microcapsules are generally quite resistant to leakage when dispersed in aqueous suspending media, and even in certain surfactant-containing media. Furthermore, when incorporated into consumer products, such as laundry detergents or conditioners, they provide perfumery benefits that are unattainable if perfume is incorporated directly into those products. However, formaldehyde is often involved in the synthesis of aminoplast resins and the presence of formaldehyde-polyamines adducts, even without the presence of substantial amount of free formaldehyde, may not be desirable in a product.

Formaldehyde-free microcapsules formed from polyurea resin, which have enhanced stability have been disclosed in EP2579976 A1 and US20130330292A1. The polyurea resin in both cases, however, is formed from aromatic polyisocyanates, which are prone to oxidation.

There remains a need to provide polyurea core shell microcapsule compositions that are useful as vehicles to encapsulate functional ingredients, such as perfume and cosmetic ingredients, which are formed by the reaction of at least one polyisocyanate, in particular at least one aliphatic polyisocyanate, and at least one polyamine and/or at least one polyimine, which display good leakage stability, even when suspended in extractive suspending media, such as liquid detergents, shampoos, and the like.

SUMMARY OF THE INVENTION

The applicant addressed the deficiencies in the prior art and found in a surprising manner that the use of a chitosan as a polyamine in the preparation of polyurea core-shell microcapsules resulted in the formation of polyurea microcapsules having superior imperviousness compared to polyurea microcapsules known to the art and being capable of stably encapsulating functional ingredients, such as perfume or cosmetic ingredients and compositions, which are particularly resistant to leakage of their core contents even when suspended in highly extractive media.

In accordance with a first aspect of the invention there is provided a composition comprising at least one core-shell microcapsule in a suspending medium, wherein said core-shell microcapsules comprise a core containing a functional ingredient, in particular a perfume and/or a cosmetic ingredient, and a shell comprising a polyurea resin formed by the reaction of at least one polyisocyanate, chitosan, and, optionally at least one other polyamine and/or polyimine, which is different from chitosan.

In one embodiment the functional ingredient is hydrophobic and the core of the core-shell capsule is in form of an oil phase (referred to as core oil in the following) that is not or only sparingly miscible with the suspending medium, which is an aqueous phase.

In one embodiment, the functional ingredient is a perfume ingredient, a perfume composition, a cosmetic ingredient, or a mixture thereof.

In accordance with a second aspect of the present invention there is provided the use of chitosan to improve the imperviousness of core-shell microcapsules and thereby their stability with respect to leakage of encapsulated functional ingredient during storage In accordance with a third aspect of the present invention there is provided a process of forming a polyurea core-shell microcapsule described above, said process comprising the steps of:
  I. Forming an oil-in-water emulsion comprising a functional ingredient-containing core oil droplet dispersed in an aqueous phase; and
  II. Reacting at least one polyisocyanate, chitosan and, optionally, at least one polyamine that is different from chitosan and/or, optionally, at least one polyimine, to form a polyurea shell around said droplet to form a core-shell microcapsule, wherein chitosan is added before, during or after the addition of said optional at least one other polyamine that is different from chitosan, and/or the optional at least one polyimine.

The chitosan may be added in step I or in step II of the process. The addition of chitosan and the addition of the optional at least one polyamine that is different from chitosan, and/or the addition of the optional at least one polyimine may be simultaneous or sequential.

In particular embodiments of any of the aspects of the invention the polyisocyanate employed in the present invention is an aliphatic polyisocyanate.

In particular embodiments of any of the aspects of the invention, the chitosan employed in the preparation of a core-shell microcapsule is in substantially unprotonated form.

In particular embodiments of any of the aspects of the invention, the chitosan employed in the preparation of core-shell microcapsule is added to the reaction medium in solid form.

The details, examples and preferences provided in relation to any particular stated aspect of the present invention will be further described herein.

DETAILED DESCRIPTION OF THE INVENTION

The present invention is based on the surprising discovery that chitosan can be employed as a polyamine co-reactant with at least one polyisocyanate in the preparation of polyurea resin core-shell microcapsules, and provide improved retention of functional ingredients, and particularly perfume ingredients or compositions contained within the microcapsule cores. The ability of chitosan to act as a co-reactant with a polyisocyanate, and its discovered core-retention effect, was to the applicant's best knowledge entirely surprising and not anticipated by the prior art.

Indeed, although the prior art does generally mention chitosan as one amongst many possible shell materials (either as an encapsulating medium, a cross-linking agent, or as a coating that can be applied onto an already formed shell to achieve a functional effect) there is no technical teaching as to how chitosan can be utilized as a shell-forming material in the formation of polyurea core-shell microcapsules, and particularly those formed using aliphatic polyisocyanates.

In particular, it is generally known that in order to form a film, chitosan must be dissolved in water at low pH and that, even under these acidic conditions, the solubility of chitosan in water is very limited, for example lower than 5 wt % or even lower than 2 wt %. Furthermore, even at such low concentrations, chitosan solutions tend to be exceedingly viscous, difficult to handle, and must be diluted as a result. Unfortunately, however, in the industrial production of core-shell microcapsules, such high dilutions cannot be contemplated for both practical and economic reasons, as slurries containing functional ingredients must be relatively rich in these ingredients in order to be effective in consumer product bases.

These facts alone would not suggest chitosan as a suitable shell-forming material even for capsules formed under pH conditions under which it shows at least limited solubility. In the context of the formation of polyurea core-shell microcapsules, the use of chitosan is even more complicated because chitosan is practically insoluble under the required alkaline conditions of capsule formation, where the reaction medium has a pH higher than 7, more particularly higher than 8 and still more particularly higher than 9; conditions where it is known that chitosan is insoluble or extremely sparingly soluble and therefore present in solid form in the slurry.

Nevertheless, despite the clear technical prejudice against the use of chitosan, the applicant surprisingly found that by adding chitosan in solid form to the reaction medium under alkaline conditions, it was possible to react chitosan with a polyisocyanate, while maintaining sufficiently high contents of microcapsules in a slurry to be industrially and economically feasible.

Furthermore, not only was it found that chitosan can be incorporated into a polyurea core-shell microcapsule as a shell-forming material, it was also found that chitosan can react with a polyisocyanate to form a polyurea core-shell microcapsule that exhibits improved retention of the encapsulated functional ingredients, compared with polyurea microcapsules conventionally formed, without chitosan, from a polyamine or polyimine and a polyisocyanate, particularly aliphatic polyisocyanate, examples of which can be found in US2016/0166480 A1. Furthermore, this improvement in stability was even observed in particularly extractive media, such as liquid detergents and shampoos.

By "extractive medium" is meant a medium in which the functional ingredients are soluble, due to the presence of high amount of surfactants and/or solvents. Surfactants that are particularly extractive include ethoxylated surfactants. Solvents that are particularly extractive include glycerol, propane-2-ol, glycol ethers and the like, The stability of compositions according to the present invention with respect to leakage in extractive bases is typically assessed by measuring the amount of functional ingredient that has leached into the base after given time, for example 1 month, at a given temperature, for example 40° C. or 45° C.

This enhanced imperviousness has been found to be the case, even when the polyisocyanate employed is aliphatic, even though these aliphatic ingredients are generally regarded to form less stable microcapsules, and compare unfavourably with aromatic polyisocyanates as a result.

Without intending to be bound by theory, it may be presumed that, under such reaction conditions, both unprotonated amine groups and, in less extent, hydroxy groups of the chitosan react with the isocyanate groups to form urea and urethane groups, thereby forming a cross-linked encapsulating polyurea/polyurethane network.

Once the chitosan has been incorporated in the shell resin, it is considered as being covalently bound to and part of the resin.

As used herein, "chitosan" refers to a biopolymer derived from chitin, forming the exoskeleton of crustaceans and preserving the shape of various fungi, such as Ascomycetes, Zygomycetes, Basidiomycetes and Deuteromycetes, for example Absidia, Mucor, Aspergillus niger, Ganoderma lucidum, Rhizopus oryzae, and the like. Chitosan production involves the alkaline or enzymatic deacetylation of chitin and is characterized by its deacetylation grade. Both low deacetylated grade, typically below 80% deacetylation, and high deacetylated grades, typically higher than or equal to 80% deacetylation, are suitable for the sake of the present invention. For example, chitosan having deacetylation grades between 60% and 100%, more particularly between 70% and 90%, and still more particularly between 75% and 85% are particularly suitable for the use in the present invention. Chitosan is available with molecular weight typically ranging from 3,000 and 1,000,000 g/mol and this range is suitable for the purpose of the present invention. Particularly suitable is the range 100,000 to 500,000 g/mol.

The present invention also relates to processes of making the core-shell microcapsules.

The microcapsules of the invention may be obtained by a process comprising at least the steps of:
I. Forming an oil-in-water emulsion comprising a functional ingredient-containing core oil droplet dispersed in an aqueous phase; and
II. Reacting at least one polyisocyanate, chitosan and, optionally, at least one other polyamine that is different from chitosan and/or, optionally, at least one polyimine, to form a polyurea shell around said droplet to form a core-shell microcapsule, wherein chitosan is added before, during or after the addition of said at least one other polyamine and/or said polyimine.

The chitosan may be added in step I or in step II of the process. The addition of chitosan may precede or follow the addition of the optional at least one other polyamine that is different from chitosan or polyimine. Both, chitosan and other polyamine and/or polyimine may be also added simultaneously in one shot or continuously during a predetermined period of time.

In a particular embodiment, the compositions of the invention are obtained by a process comprising the steps of
1) Mixing together a core oil containing a functional ingredient and the at least one polyisocyanate with a water phase containing an emulsifier, wherein the water phase has a pH of 7 or higher, more particularly 8 or higher, and still more particularly a pH of between about 8.5 and 9.5, thereby to obtain an oil-in-water emulsion;
2) Adding at least one other polyamine to the emulsion, provided that the polyamine is not chitosan and/or adding at least one polyimine;
3) Increasing temperature of the emulsion containing the polyamine to an elevated temperature that is at least about 50° C., more particularly at least about 70° C., and still more particularly between about 75° C. and 95° C., to initiate the reaction of polyisocyanate and polyamine or polyimine to form a slurry of nascent microcapsules;
4) Adding chitosan in the form of a powder to the slurry of nascent microcapsules and maintaining the temperature for a period of at least about 30 minutes, more particularly at least about 1 hour, more particularly at least about 2 hours to form a slurry of microcapsules before cooling.

In the context of the present invention, the term "nascent" as it refers to the core-shell microcapsules is used to describe microcapsules that are in the process of being formed and where the shell-forming process is taking place, whether the process is one or more of interfacial polymerization, polyaddition, polycondensation, radical polymerization, ring-opening polymerization, or the like. In the shell-forming process, the locus of the polymerization, as the term is used herein, is the oil-water interface between the core oil droplets from the aqueous dispersion medium. Usually, this interface is stabilized by surfactants or polymeric emulsifiers.

The so-formed slurry of microcapsules may be additionally treated with a preservative to protect the slurry from microbial contamination. Additional treatment may also include the addition of a suspending agent, such as a hydrocolloid, in order to assist the suspension of the microcapsules in the slurry and prevent the microcapsules from creaming or sedimentation.

In carrying out step 1) of the process the mixing apparatus and speed of mixing may be controlled in a manner known per se, in order to provide any desired droplet size. Typically, the emulsion is formed at a stirring speed within an interval of 100 to 2000 rpm, more particularly more particularly from 250 to 1500 rpm, and still more particularly from 500 rpm to 1000 rpm for a vessel having a volume of 1 liter, equipped with a cross-beam stirrer with pitched bean, and having a stirrer diameter to reactor diameter 0.7. The stirrer apparatus may comprise a turbine, a Mig stirrer, and the like. The person skilled in the art will however easily understand that such stirring conditions may change depending on the size of the reactor and of the volume of the slurry, on the exact geometry of the stirrer on the ratio of the diameter of the stirrer to the diameter of the reactor diameter ratios. For example, for a Mig stirrer with stirrer to reactor diameter ratio from 0.5 to 0.9 and slurry volumes ranging from 0.5 to 8 tons, the preferable agitation speed in the context of the present invention is from 150 rpm to 50 rpm.

In carrying out steps 2) and 3) of the process, the at least one other polyamine or polyimine may be added to the emulsion at ambient temperature, before the temperature is increased to the elevated temperature interval in order to initiate preparation of the nascent microcapsules. Alternatively, however, the emulsion may already be at the required elevated temperature before the optional at least one other polyamine and/or the optional at least one polyimine is added, and indeed, said at least one other polyamine and/or polyimine may be at ambient temperature or at an elevated temperature when it is added to the emulsion.

In carrying out step 4) of the process, the amount of chitosan that can be added to the reaction mixture is preferably between about 0.05 and about 2 wt % of chitosan, more particularly between about 0.1 and about 1 wt %, based on the total weight of the slurry. The entire amount of chitosan may be added in one operation, or it can be added portion-wise in a series of steps.

In accordance with the process of the present invention, it is possible to form slurries of core-shell microcapsules, wherein the microcapsules can retain more than 80 wt % of an encapsulated perfume composition during storage periods up to 30 days at 45° C. in an extractive base, such as a shampoo or a liquid detergent.

A considerable advantage of the use of chitosan in solid form is that in no instance dilution of the system occurs and, accordingly, the solid content of the slurry can be maintained at high levels. Accordingly, a slurry according to the present invention may have a solid content of from 10 to 50 weight percent (wt %), more particularly 25 to 48 wt %, and still more particularly 35 to 45 wt %.

In the present context, the solid content of the slurry is determined experimentally by measuring the weight of this slurry before and after drying on a thermo-balance operating at 120° C. The weight of the dry slurry is taken at the point where the rate of weight loss is below 0.1 wt %/min, referred to the initial weight of wet slurry deposited on the thermo-balance. The solid content is taken as a measure of the amount of microcapsules present in the slurry and is expressed as in weight percentage of the wet slurry.

The microcapsules can have a shell to core weight ratio of 0.05 to 0.40, more particularly 0.1 to 0.35, and still more particularly 0.15 to 0.30, wherein the shell to core weight ratio is defined as the ratio of the sum of the weight percentages of all components of the shell involved in the process, meaning polyisocyanates, polyamines and/or polyimines including chitosan and emulsifier, to the weight percentage of the core oil, wherein all weight percentages refer to the total weight of the slurry.

The shell material may be composed of a resin which can contain from about 0.1 to about 20 wt %, more particularly from about 0.5 to about 10 wt % and still more particularly from 0.8 to 5 wt % of moieties derived from chitosan, referred to the total weight of the polyurea resin, meaning the total weight of the polyisocyanates and polyamines and/or polyimines, including chitosan, involved in the encapsulation process and disregarding any emulsifier present.

The shell material may be composed of resin which can contain from about 0 to about 30 wt %, more particularly from about 10 to about 20 wt % of moieties derived from at least one other or more polyamines that are not chitosan, and/or polyimines, referred to the total weight of the polyurea resin, meaning the total weight of the polyisocyanates and polyamines and/or polyimines, including chitosan, involved in the encapsulation process, and disregarding any emulsifier present.

The shell material may be composed of resin which can contain 50 to 95 wt %, more particularly from 80 to 90 wt %, of moieties derived from one or more polyisocyanates, and particularly aliphatic polyisocyanates, referred to the total weight of the polyurea resin, meaning the total weight of the polyisocyanates, polyamines and/or polyimines, including chitosan, involved in the encapsulation process, and disregarding any emulsifier present.

The shell material can contain from 5 to 50 wt %, more particularly from 10 to 40 wt %, still more particularly from 15 to 35 wt % of one or more emulsifiers employed in the preparation of the oil-in-water emulsion, based on the total weight of the shell including the emulsifier.

The term "moiety" or "moieties" as used herein refers to a component of the resin, which is a residue of chitosan or of the polyamine, or of the polyisocyanate, and which derives from the reaction of chitosan, the polyamine, the polyimine or the polyisocyanate during the formation of the resin.

Polyisocyanates useful in the context of the present invention include any of the known aliphatic or aromatic polyisocyanates that have been described as shell-forming materials for encapsulated perfumery.

Aliphatic polyisocyanates useful in the context of this invention may be selected from the group comprising 1,6-diisocyanatohexane (CAS No. 822-06-0), 1,5-diisocyanato-2-methylpentane (CAS No. 34813-62-2), 1,4-diisocyanato-2,3-dimethylbutane, 2-ethyl-1,4-diisocyanatobutane, 1,5-diisocyanatopentane (CAS No. 4538-42-5), 1,4-diisocyanatobutane (CAS No. 4538-37-8), 1,3-diisocyanatopropane (CAS No. 3753-93-3), 1,10-diisocyanatodecane (CAS No. 538-39-0), 1,2-diisocyanatocyclobutane, bis(4-isocyanatocyclohexyl)methane (CAS No. 5124-30-1, commercially available under the Trade Name DESMODUR® W), 3,3,5-trimethyl-5-isocyanatomethyl-1-isocyanatocyclohexane (CAS No. 4098-71-9), 2-Imidodicarbonic diamide (CAS No. 4035-89-6), biuret (CAS No. 108-19-0), aliphatic polyisocyanate based on hexamethylene diisocyanate and alkylene oxide, especially ethylene oxide, (sold under the name BAYHYDUR), for example Bayhydur® XP 2547 (commercially available from Bayer); and mixtures thereof.

The at least one other polyamine, in addition to chitosan, useful in the present invention may be selected from the group comprising 1,2-ethylenediamine; 1,3-diaminopropane; 1,4-diaminobutane; 1,6-diaminohexane; hydrazine; 1,4-diaminocyciohexane; 1,3-diamino-1-methylpropane; diethylenetriamine; triethylenetetramine; bis(2-methylaminoethyl)ether (CAS No. 3033-62-3), guanidine (CAS No. 113-00-8); guanidine carbonate salt (CAS No. 593-85-1); 3,5-Diamino-1,2,4-triazole (CAS No. 1455-77-2); 2,4,6-Diamino-1,3,5-triazole (CAS No. 108-78-1); urea; polymeric polyamines; and mixtures thereof.

Polymeric polyamines also useful for the sake of the present invention may be selected from the group comprising: poly(vinylamine), such as those available commercially under the trade name LUPAMINE (ex BASF); poly(etheramine), such as those available commercially under the trade name JEFFAMINE (ex Huntsman); and mixtures thereof. These polymeric polyamines may have two functions: on one hand these materials may react with the polyisocyanate to form polyurea resin and, on the other hand, to act as an emulsifier making the dispersion of the core material into the water phase easier.

Alternatively, also polyimines can be useful in the present invention, for example poly(ethyleneimine) (CAS No. 9002-98-6)), such as those available commercially under the trade name LUPASOL (ex BASF).

The product of a polyamine with formaldehyde, also referred to as methylolated polyamine condensate, or the polycondensation product of a polyamine with formaldehyde or the polycondensation product of methylolated polyamines, also referred to as aminoplast resins that contains free amines are also useful for the sake of the present invention. If a polyamine condensate, or a polycondensation product of a polyamine with formaldehyde or a polycondensation product of methylolated polyamines is employed and contains free amines, then the residue of such a material that reacts in a shell-forming reaction is considered to be a polyamine. The presence of free amines may be assessed by techniques known to the art.

The polyamines and polyimines are provided in the water phase of the emulsion prior to and/or during the encapsulation process. As in the case of chitosan, the amine groups of the polyamines and of the polyimines react with the isocyanate groups to form urea groups, thereby forming a cross-linked encapsulating polyurea network.

In a preferred embodiment, the aqueous phase comprises at least one emulsifier, wherein said at least one emulsifier is selected from the group comprising non-ionic surfactants, ionic surfactants and polymeric emulsifiers, also known under the term "protective colloids".

Polymer emulsifiers that are especially useful for the sake of the present invention may be selected from the group comprising partially hydrolysed poly(vinyl acetate), such as polyvinyl alcohols having a degree of hydrolysis between 80% and 99%, for example 88% or 96%; poylvinylpyrrolidone (also known as poly(1-vinylpyrrolidin-2-one)); poly(sodium4-styrenesulfonate); and the like.

In a preferred embodiment, the emulsifier is polyvinylpyrrolidone (PVP) having a K-value of more than 40, preferably 60 and a molecular weight of more than 150,000 g/mol, preferably from 350,000 to 500,000 g/mol.

The K-values assigned to various grades of PVP polymer represent a function of the average molecular weight, the degree of polymerization and the intrinsic viscosity. The K-values are derived from viscosity measurements and are calculated according to Fikentscher's formula (see for example M. Alger, Polymer Science Dictionary, Chapman & Hall, 1997, ISBN 0 412 608707, page 196).

In one embodiment, the core oil consists of at least one functional ingredient.

In another embodiment, the core oil comprises at least one functional ingredient and an adjuvant, such as a solvent, an oil, a wax, a surfactant, a polymer, and the like, and a mixture thereof.

The functional ingredients may include fragrance or perfume ingredients, fragrance or perfume compositions (the terms fragrance and perfume being synonymous), pesticides, catalysts, pheromones, functional cosmetic ingredients and the like.

In an embodiment of the invention, the core oil comprises at least one perfume ingredient. A comprehensive list of perfume ingredients that may be encapsulated in accordance with the present invention may be found in the perfumery literature, for example "Perfume & Flavor Chemicals", S. Arctander (Allured Publishing, 1994), as well as later editions of this work, which are herein incorporated by reference. Encapsulated perfume according to the present invention comprise preferably perfume ingredients selected from ADOXAL (2,6,10-trimethylundec-9-enal); AGRUMEX (2-(tert-butyl)cyclohexyl acetate); ALDEHYDE C 10 DECYLIC (decanal); ALDEHYDE C 11 MOA (2-methyldecanal); ALDEHYDE C 11 UNDECYLENIC (undec-10-enal); ALDEHYDE C 110 UNDECYLIC (undecanal); ALDEHYDE C 12 LAURIC (dodecanal); ALDEHYDE C 12 MNA PURE (2-methylundecanal); ALDEHYDE ISO C 11 ((E)-undec-9-enal); ALDEHYDE MANDARINE 10%/TEC ((E)-dodec-2-enal); ALLYL AMYL GLYCOLATE (allyl 2-(isopentyloxy)acetate); ALLYL CYCLOHEXYL PROPIONATE (allyl 3-cyclohexylpropanoate); ALLYL OENANTHATE (allyl heptanoate); AMBER CORE (1-((2-(tert-butyl)cyclohexyl)oxy)butan-2-ol); AMBERMAX (1,3,4,5,6,7-hexahydro-.beta.,1,1,5,5-pentamethyl-2H-2,4a-Methanonaphthalene-8-ethanol); AMYL SALICYLATE (pentyl 2-hydroxybenzoate); APHERMATE (1-(3,3-dimethylcyclohexyl)ethyl formate); BELAMBRE ((1R,2S,4R)-2T-isopropyl-1,7,7-trimethylspiro[bicyclo[2.2.1]heptane-2,4'-[1,3]dioxane]); BIGARYL (8-(sec-butyl)-5,6,7,8-tetrahydroquinoline); BOISAMBREN E FORTE ((ethoxymethoxy)cyclododecane); BOISIRIS ((1S,2R,5R)-2-ethoxy-2,6,6-trimethyl-9-methylenebicyclo[3.3.1]nonane); BORNYL ACETATE ((2S,4S)-1,7,7-trimethylbicyclo[2.2.1]heptan-2-yl acetate); BUTYL BUTYRO LACTATE (1-butoxy-1-oxopropan-2-yl butyrate); BUTYL CYCLOHEXYL ACETATE PARA (4-(tert-butyl)cyclohexyl acetate); CARYOPHYLLEN E ((Z)-4,11,11-trimethyl-8-methylene bicyclo[7.2.0]undec-4-ene); CASHMERAN (1,1,2,3,3-pentamethyl-2,3,6,7-tetrahydro-1H-inden-4(51-1)-one); CASSYRANE (5-tert-butyl-2-methyl-5-propyl-2H-furan); CITRAL ((E)-3,7-dimethylocta-2,6-dienal); CITRAL LEMAROME N ((E)-3,7-dimethylocta-2,6-dienal); CITRATHAL R ((Z)-1,1-diethoxy-3,7-dimethylocta-2,6-diene); CITRONELLAL (3,7-dimethyloct-6-enal); CITRONELLOL (3,7-dimethyloct-6-en-1-ol); CITRONELLYL ACETATE (3,7-dimethyloct-6-en-1-yl acetate); CITRONELLYL FORMATE (3,7-dimethyloct-6-en-1-yl formate); CITRONELLYL NITRILE (3,7-dimethyloct-6-enenitrile); CITRONELLYL PROPIONATE (3,7-dimethyloct-6-en-1-yl propionate); CLONAL (dodecanenitrile); CORANOL (4-cyclohexyl-2-methylbutan-2-ol); COSMONE ((Z)-3-methylcyclotetradec-5-enone); CYCLAMEN ALDEHYDE (3-(4-isopropylphenyl)-2-methylpropanal); CYCLOGALBANATE (allyl 2-(cyclohexyloxy)acetate); CYCLOHEXYL SALICYLATE (cyclohexyl 2-hydroxybenzoate); CYCLOMYRAL (8,8-dimethyl-1,2,3,4,5,6,7,8-octahydronaphthalene-2-carbaldehyde); DAMASCENONE ((E)-1-(2,6,6-trimethylcyclohexa-1,3-dien-1-yl)but-2-en-1-one); DAMASCONE ALPHA ((E)-1-(2,6,6-trimethylcyclohex-2-en-1-yl)but-2-en-1-one); DAMASCONE DELTA ((E)-1-(2,6,6-trimethylcyclohex-3-en-1-yl)but-2-en-1-one); DECENAL-4-TRANS ((E)-dec-4-enal); DELPHONE (2-pentylcyclopentanone); DIHYDRO ANETHOLE (propanedioic acid 1-(1-(3,3-dimethylcyclohexyl)ethyl) 3-ethyl ester); DIHYDRO JASMONE (3-methyl-2-pentylcyclopent-2-enone); DIMETHYL BENZYL CARBINOL (2-methyl-1-phenylpropan-2-ol); DIMETHYL BENZYL CARBINYL ACETATE (2-methyl-1-phenylpropan-2-yl acetate); DIMETHYL BENZYL CARBINYL BUTYRATE (2-methyl-1-phenylpropan-2-yl butyrate); DIMETHYL OCTENONE (4,7-dimethyloct-6-en-3-one); DIMETOL (2,6-dimethylheptan-2-ol); DIPENTENE (1-methyl-4-(prop-1-en-2-yl)cyclohex-1-ene); DUPICAL ((E)-4-((3aS,7aS)-hexahydro-1H-4,7-methanoinden-5(6H)-ylidene)butanal); EBANOL ((E)-3-methyl-5-(2,2,3-trimethylcyclopent-3-en-1-yl)pent-4-en-2-ol); ETHYL CAPROATE (ethyl hexanoate); ETHYL CAPRYLATE (ethyl octanoate); ETHYL LINALOOL ((E)-3,7-dimethylnona-1,6-dien-3-ol); ETHYL LINALYL ACETATE ((Z)-3,7-dimethylnona-1,6-dien-3-yl acetate); ETHYL OENANTHATE (ethyl heptanoate); ETHYL SAFRANATE (ethyl 2,6,6-trimethylcyclohexa-1,3-diene-1-carboxylate); EUCALYPTOL ((1s,4s)-1,3,3-trimethyl-2-oxabicyclo[2.2.2]octane); FENCHYL ACETATE ((2S)-1,3,3-trimethylbicyclo[2.2.1]heptan-2-yl acetate); FENCHYL ALCOHOL ((1S,2R,4R)-1,3,3-trimethylbicyclo[2.2.1]heptan-2-ol); FIXOLIDE (1-(3,5,5,6,8,8-hexamethyl-5,6,7,8-tetrahydronaphthalen-2-yl)ethanone); FLORALOZONE (3-(4-ethylphenyl)-2,2-dimethylpropanal); FLORHYDRAL (3-(3-isopropylphenyl)butanal); FLOROCYCLENE ((3aR,6S,7aS)-3a,4,5,6,7,7a-hexahydro-1H-4,7-methanoinden-6-yl propionate); FLOROPAL (2,4,6-trimethyl-4-phenyl-1,3-dioxane); FRESKOMENTHE (2-(sec-butyl)cyclohexanone); FRUITATE ((3aS,4S,7R,7aS)-ethyl octahydro-1H-4,7-methanoindene-3a-carboxylate); FRUTONILE (2-methyldecanenitrile); GALBANONE PURE (1-(3,3-dimethylcyclohex-1-en-1-yl)pent-4-en-1-one); GARDOCYCLENE ((3aR,6S,7aS)-3a,4,5,6,7,7a-hexahydro-1H-4,7-methanoinden-6-yl isobutyrate); GERANIOL ((E)-3,7-dimethylocta-2,6-dien-1-ol); GERANYL ACETATE SYNTHETIC ((E)-3,7-dimethylocta-2,6-dien-1-yl acetate); GERANYL ISOBUTYRATE ((E)-3,7-dimethylocta-2,6-dien-1-yl isobutyrate); GIVESCONE (ethyl 2-ethyl-6,6-dimethylcyclohex-2-enecarboxylate); HABANOLIDE ((E)-oxacyclohexadec-12-en-2-one); HEDIONE (methyl 3-oxo-2-pentylcyclopentaneacetate); HERBANATE ((2S)-ethyl 3-isopropylbicyclo[2.2.1]hept-5-ene-2-carboxylate); HEXENYL-3-CIS BUTYRATE ((Z)-hex-3-en-1-yl butyrate); HEXYL CINNAMIC ALDEHYDE ((E)-2-benzylideneoctanal); HEXYL ISOBUTYRATE (hexyl isobutyrate); HEXYL SALICYLATE (hexyl 2-hydroxybenzoate); INDOFLOR (4,4a,5,9b-tetrahydroindeno[1,2-d][1,3]dioxine); IONONE BETA ((E)-4-(2,6,6-trimethylcyclohex-1-en-1-yl)but-3-en-2-one); IRISONE ALPHA ((E)-4-(2,6,6-trimethylcyclohex-2-en-1-yl)but-3-en-2-one); IRONE ALPHA ((E)-4-(2,5,6,6-tetramethylcyclohex-2-en-1-yl)but-3-en-2-one); ISO E SUPER (1-(2,3,8,8-tetramethyl-1,2,3,4,5,6,7,8-octahydronaphthalen-2-yl)ethanone); ISOCYCLOCITRAL (2,4,6-trimethylcyclohex-3-enecarbaldehyde); ISONONYL ACETATE (3,5,5-trimethylhexyl acetate); ISOPROPYL METHYL-2-BUTYRATE (isopropyl 2-methyl butanoate); ISORALDEINE 70 ((E)-3-methyl-4-(2,6,6-trimethylcyclohex-2-en-1-yl)but-3-en-2-one); JASMACYCLENE ((3aR,6S,7aS)-3a,4,5,6,7,7a-hexahydro-1H-4,7-methanoinden-6-yl acetate); JASMONE CIS ((Z)-3-methyl-2-(pent-2-en-1-yl)cyclopent-2-enone); KARANAL (5-(sec-butyl)-2-(2,4-dimethylcyclohex-3-en-1-yl)-5-methyl-1,3-dioxane); KOAVONE ((Z)-3,4,5,6,6-pentamethylhept-3-en-2-one); LEAF ACETAL ((Z)-1-(1-ethoxyethoxy)hex-3-ene); LEMONILE ((2E,6Z)-3,7- dimethylnona-2,6-dienenitrile); LIFFAROME GIV ((Z)-hex-3-en-1-yl methyl carbonate); LILIAL (3-(4-(tert-butyl)phenyl)-2-methylpropanal); LINALOOL (3,7-dimethylocta-1,6-dien-3-ol); LINALYL ACETATE (3,7-dimethylocta-1,6-dien-3-yl acetate); MAHONIAL ((4E)-9-hydroxy-5,9-dimethyl-4-decenal); MALTYL ISOBUTYRATE (2-methyl-4-oxo-4H-pyran-3-yl isobutyrate); MANZANATE (ethyl 2-methylpentanoate); MELONAL (2,6-dimethylhept-5-enal); MENTHOL (2-isopropyl-5-methylcyclohexanol); MENTHONE (2-isopropyl-5-methylcyclohexanone); METHYL CEDRYL KETONE (1-((1S,8aS)-1,4,4,6-tetramethyl-2,3,3a,4,5,8-hexahydro-1H-5,8a-methanoazulen-7-yl)ethanone); METHYL NONYL KETONE EXTRA (undecan-2-one); METHYL OCTYNE CARBONATE (methyl non-2-ynoate); METHYL PAMPLEMOUSSE (6,6-dimethoxy-2,5,5-trimethylhex-2-ene); MYRALDENE (4-(4-methylpent-3-en-1-yl)cyclohex-3-enecarbaldehyde); NECTARYL (2-(2-(4-methylcyclohex-3-en-1-yl)propyl)cyclopentanone); NEOBERGAMATE FORTE (2-methyl-6-methyleneoct-7-en-2-yl acetate); NEOFOLIONE ((E)-methyl non-2-enoate); NEROLIDYLE ((Z)-3,7,11-trimethyldodeca-1,6,10-trien-3-yl acetate); NERYL ACETATE HC ((Z)-3,7-dimethylocta-2,6-dien-1-yl acetate); NONADYL (6,8-dimethylnonan-2-ol); NONENAL-6-CIS ((Z)-non-6-enal); NYMPHEAL (3-(4-isobutyl-2-methylphenyl)propanal); ORIVONE (4-(tert-pentyl)cyclohexa none); PARADISAMIDE (2-ethyl-N-methyl-N-(m-tolyl)butanamide); PELARGENE (2-methyl-4-methylene-6-phenyltetrahydro-2H-pyran); PEONILE (2-cyclohexylidene-2-phenylacetonitrile); PETALIA (2-cyclohexylidene-2-(o-tolyl)acetonitrile); PIVAROSE (2,2-dimethyl-2-pheylethyl propanoate); PRECYCLEMONE B (1-methyl-4-(4-methylpent-3-en-1-yl)cyclohex-3-enecarbaldehyde); PYRALONE (6-(sec-butyl)quinoline); RADJANOL SUPER ((E)-2-ethyl-4-(2,2,3-trimethylcyclopent-3-en-1-yl)but-2-en-1-ol); RASPBERRY KETONE (N112) (4-(4-hydroxyphenyl)butan-2-one); RHUBAFURANE (2,2,5-trimethyl-5-pentylcyclopentanone); ROSACETOL (2,2,2-trichloro-1-phenylethyl acetate); ROSALVA (dec-9-en-1-ol); ROSYFOLIA ((1-methyl-2-(5-methylhex-4-en-2-yl) cyclopropyl)-methanol); ROSYRANE SUPER (4-methylene-2-phenyltetrahydro-2H-pyran); SERENOLIDE (2-(1-(3,3-dimethylcyclohexyl)ethoxy)-2-methylpropyl cyclopropanecarboxylate); SILVIAL (3-(4-isobutylphenyl)-2-methylpropanal); SPIROGALBANONE (1-(spiro [4.5]dec-6-en-7-yl)pent-4-en-1-one); STEMONE ((E)-5-methylheptan-3-one oxime); SUPER MUGUET ((E)-6-ethyl-3-methyloct-6-en-1-ol); SYLKOLIDE ((E)-2-((3,5-dimethylhex-3-en-2-yl)oxy)-2-methylpropyl cyclopropanecarboxylate); TERPINENE GAMMA (1-methyl-4-propan-2-ylcyclohexa-1,4-diene); TERPINOLENE (1-methyl-4-(propan-2-ylidene)cyclohex-1-ene); TERPINYL ACETATE (2-(4-methylcyclohex-3-en-1-yl) propan-2-yl acetate); TETRAHYDRO LINALOOL (3,7-dimethyloctan-3-ol); TETRAHYDRO MYRCENOL (2,6-dimethyloctan-2-ol); THIBETOLIDE (oxacyclohexadecan-2-one); TRIDECENE-2-NITRILE ((E)-tridec-2-enenitrile); UNDECAVERTOL ((E)-4-methyldec-3-en-5-ol); VELOUTONE (2,2,5-trimethyl-5-pentylcyclopentanone); VIRIDINE ((2,2-dimethoxyethyl)benzene); ZINARINE (2-(2,4-dimethylcyclohexyl)pyridine); and mixture thereof.

In an embodiment of the invention, the core oil comprise at least one functional cosmetic ingredient. The functional cosmetic ingredients for use in the encapsulated compositions are preferably hydrophobic. Preferably, the functional cosmetic ingredients have a calculated octanol/water partition coefficient (ClogP) of 1.5 or more, more preferably 3 or more. Preferably, the ClogP of the functional cosmetic ingredients is from about 2 to about 7.

Particularly useful functional cosmetic ingredients may be selected from the group consisting of emollients, smoothening ingredients, hydrating ingredients, soothing and relaxing ingredients, decorative ingredients, deodorants, anti-aging ingredients, cell rejuvenating ingredients, draining ingredients, remodelling ingredients, skin levelling ingredients, preservatives, anti-oxidants, antibacterial or bacteriostatic ingredients, cleansing ingredients, lubricating ingredients, structuring ingredients, hair conditioning ingredients, whitening ingredients, texturing ingredients, softening ingredients, anti-dandruff ingredients, and exfoliating ingredients.

Particularly useful functional cosmetic ingredients include, but are not limited to hydrophobic polymers, such as alkyldimethylsiloxanes, polymethylsilsesquioxanes, polyethylene, polyisobutylene, styrene-ethylene-styrene and styrene-butylene-styrene block copolymers, and the like; mineral oils, such as hydrogenated isoparaffins, silicone oils and the like; vegetable oils, such as argan oil, jojoba oil, aloe vera oil, and the like; fatty acids and fatty alcohols and their esters; glycolipids; phospholipides; sphingolipides, such as ceramides; sterols and steroids; terpenes, sesquiterpenes, triterpenes and their derivatives; essential oils, such as Arnica oil, Artemisia oil, Bark tree oil, Birch leaf oil, Calendula oil, Cinnamon oil, Echinacea oil, Eucalyptus oil, Ginseng oil, Jujube oil, Helianthus oil, Jasmine oil, Lavender oil, Lotus seed oil, Perilla oil, Rosemary oil, Sandal wood oil, Tea tree oil, Thyme oil, Valerian oil, Wormwood oil, Ylang Ylang oil, Yucca oil and the like.

In an embodiment, the functional cosmetic ingredient may be selected from the group consisting of Sandal wood oil, such as Fusanus Spicatus kernel oil; Panthenyl triacetate (CAS-No: 94089-18-6); Tocopheryl acetate; Tocopherol; Naringinin; Ethyl linoleate; Farnesyl acetate; Farnesol; Citronellyl methyl crotonate (CAS-No: 20770-40-5); Ceramide-2 (1-Stearoyl-C18-Sphingosine, CAS-No: 100403-19-8); and mixtures thereof.

Should a suspending agent be employed to stably suspend the microcapsules in a slurry, suitable hydrocolloids may be employed. Suitable hydrocolloids include starch and starch derivatives, such as modified starch, dextrin, maltodextrin; gums, such as gum Arabic or gum acacia, xanthan gum, gum tragacanth, gum karaya, guar gum; cellulose and cellulose derivatives, such as carboxy methyl cellulose, hydroxyethyl cellulose, hydroxyethyl cellulose/lauryl-dimethylammoniumepoxy condensat, hydroxypopyl cellulose, cationic cellulose (for example Polyquaternium-4), cellulose gum; carrageenan; agar-agar; pectines and pectic acid; gelatine; protein hydrolysates; polymer and copolymers of vinyl and allyl monomers, such as polyvinylpyrrolidone; poly(vinyl pyrrolidone-co-vinylacetate); poly(vinyl alcohol-co-vinyl acetate), more particularly hydrolyzed polyvinylacetates having a degree of hydrolysis between 85 and 92%; vinyl ester homopolymers and copolymers, such as vinyl acetate, vinyl pivalate, vinyl versatate; poly(vinyl methyl ether), poly(vinyl alkyl amines), such as poylvinylmethylamine; quaternized polyvinyl alkyl amines, vinyl pyridine and quaternized vinyl pyridine, vinyl imidazoline, vinyl imidazole, vinyl imidazolinium, dimethyldiallyl ammonium chloride; and vinyl sulphonate homopolymers and copolymers; polyamines and polyimines; ethoxylated polyamines; polymers, copolymers and cross-polymers derived from (meth) acryloyl monomers, such as methyl methacrylate, ethyl methacrylate, 2-ethyl-hexyl acrylate, lauryl methacrylate, C10-C30 alkyl acrylate, and the like, hydroxyalkyl (meth)

acrylate, such as 2-hydroxypropyl acrylate and 2-hydroxypropyl methacrylate, and the like; acrylamidodimethyl taurate; aryl (meth)acrylates, such as phenyl acrylate and benzyl acrylate, (meth)acrylic acids and their salts, such as sodium and potassium (meth)acrylates, sodium acryloyldimethyltaurate; (meth)acrylamides; N-alkyl (meth)acrylamides, such as N,N-dimethylaminoalkyl methacrylate; quaternized N-alkyl (meth)acrylamides, such as methacrylamidopropyl-trimethylammonium chloride; acrylamidoe-thyltrimonium chloride; acrylamidolauryltrimethylammonium chloride; and (meth)acrylamido alkyl sulphonates poly(maleic anhydride) and poly(maleic anhydride-co-vinyl ether), and their hydrolysates; poly(acrylic acid-co-maleic acid)copolymer; poly(alkyleneoxide); polyurethanes and polyureas, such as anionic, cationic non-ionic and amphoteric polyurethanes and polyureas; mixed copolymers thereof; and mixture thereof.

Should it be desired to employ preservatives to guard against microbial contamination, suitable preservatives for the purpose includes but are not limited to quaternary compounds, biguanide compounds (CAS #: 32289-58-0/27083-27-8/28757-47-3/133029-32-0), poylaminopropyl biguanidine, Hexetidine, para-chloro-meta-cresol, methenamine, 3-Bis(hydroxymethyl)-5,5-dimethylimidazolidine-2,4-dione, Quaternium-15, benzoic acid, salicylic acid, undec-10-enoic acid, formic acid, biphenyl-2-ol and their salts, 4-hydroxybenzoic acid and its esters and salts; sorbic acid and its salts, Isothiazolinones, Bronopol (2-Bromo-2-nitro-1,3-propanediol), 5-bromo-5-nitro-1,3-dioxane, Thiabendazone, Benzimidazole carbamate, Triclocarban; 3-Iodo-2-propynylbutylcarbamate, Thiomersal; Triclosan, dichlorobenzyl alcohol, chloroxylenol, imidazolidinyl urea, phenoxyethanol, benzyl alcohol; and mixture thereof.

In an embodiment, chitosan is used as biological preservative, and the slurry is substantially free of any additional biological preservative.

The slurry may also contain other commonly employed adjuvants. The term "adjuvants" refers to ingredients that may affect the performance of a slurry, other than its hedonic performance. For example, an adjuvant may be an ingredient that acts as an aid to processing a perfume composition or consumer product containing said composition, or it may improve handling or storage of a perfume composition or consumer product. It might also be an ingredient that provides additional benefits such as imparting colour or texture. It might also be an ingredient that imparts light resistance or chemical stability to one or more ingredients contained in a perfume composition or consumer product. A detailed description of the nature and type of adjuvants commonly used in perfume compositions or consumer products cannot be exhaustive, but such ingredients are well known to a person skilled in the art. Examples of adjuvants include solvents, waxes, oils, pigments, dyestuffs and colouring matters; extenders, fillers and reinforcing agents; stabilizers against the detrimental effects of heat and light, bulking agents, acidulants, buffering agents and antioxidants.

If it is desired to isolate the microcapsules in the form of a dry powder, a slurry may be spray dried in a further step. Prior to the spray drying step, it may be desirable to add a flow aid, such as silica or the like to the slurry to ensure the realization of fine, free-flowing powdered microcapsules with low surface perfume oil.

The resulting slurry of microcapsules may be spray-dried in a conventional spray drying tower, using a two-fluid nozzle, or spin-dried in a conventional spin dryer. If desired, at least one hydrocolloid may be added to the microcapsule slurry, as such or in the form of an aqueous solution. Typical hydrocolloids include starch, modified starch such as dextrin-modified with octenyl succinate anhydride, and gum Arabic. Optionally, maltodextrins and sugar alcohols, such as sorbitol, mannitol or maltitol may also be added. The hydrocolloid may itself contain a functional ingredient. This functional ingredient may be the same as, or different form, that in the capsule. This is achieved by performing the step of (1) emulsifying a second functional ingredient in aqueous hydrocolloid solution, optionally comprising maltodextrins and sugars or sugar alcohols to form a second slurry (2) mixing the second slurry with a slurry of microcapsules comprising a first functional ingredient and (3) drying this mixture. Such a process is described in WO 2007137441 A1, Example 5, which is taken herein as reference.

In a particular embodiment, the suspending medium comprising the core-shell microcapsules according to the present invention is a hydrophilic matrix comprising one or more hydrocolloids, optionally one or more maltodextrins and optionally one or more functional ingredients that may be identical, similar or different from the functional ingredient encapsulated in the core-shell microcapsules.

The compositions of the present invention may be used to perfume all manners of consumer products, including laundry care detergents, laundry care conditioners, fabric refreshers, personal care cleansing compositions, such as shampoos, bath and shower gels, liquid soaps, soap bars and the like, personal care conditioning composition, such as hair care conditioners, bath and shower lotions, deodorant compositions, antiperspirant compositions, home care compositions, such as hard surface cleaners, heavy duty detergents and the like.

Typical consumer products concerned by the present invention include personal care cleaning and cleansing compositions, such as shampoos, bath and shower gels, liquid soaps, soap bars and the like, laundry care products, such as detergents, and home care products, such as hard surface cleaners.

The consumer products according to the present invention may be used for treating substrates, such as fabrics, skin, hair, animate and inanimate surfaces, hard surfaces and the like, wherein the action of treating a substrate includes washing, cleansing, softening, caring, finishing, scenting and/or deodorizing this substrate.

In one aspect of the invention, a consumer product contains the compositions according to the present invention preferably at a level of about 0.02 to 5 wt %, more particularly from about 0.1 to 2 wt % and still more particularly from about 0.2 to 1 wt % of the consumer product.

In many cases, the consumer products concerned by the present invention contain surfactants, such as anionic, cationic, amphoteric or non-ionic surfactants.

The consumer products concerned by the present invention may contain acids or bases, or substances providing acidity or alkalinity, also referred to as acidity sources or alkalinity sources.

The consumer products concerned by the present invention may contain builders for reducing water hardness, such as phosphates, polyphosphates, polycarboxylates, sodium citrate, sodium carbonate, sodium silicate, sodium aluminosilicate (zeolite), and the like.

In many cases, the consumer products concerned by the present invention are liquid and may contain further additives, such as solvents, fillers, texturing agents, such as thickener and rheological aids, distributing aids, anti-redeposition agents, preservative agents, deodorizing agents, cosmetic ingredients, surface enhancing agents, The consumer product containing microcapsules of the present invention may contain at least one solvent selected from water-soluble solvents, or water-insoluble, or partially water-soluble solvents.

The consumer product containing microcapsules of the present invention may contain at least one texturing agent and/or colloid stabilizer, selected from rheology modifiers, thickener, gel-forming agents, thixotropic agents, and dispersing agents.

The consumer product containing microcapsules of the present invention may contain at least one silicone, selected from, but not limited to dimethicone, poly(dimethylsiloxabedimethylsiloxane), amino-silicone, such as amodimethiocone, trialkylammonium-silicone salts, ethoxylated silicones and the like.

The consumer product containing microcapsules of the present invention may contain at least one cosmetic ingredient selected from, but not limited to emollients, moisturizing agents, anti-wrinkle agents, exfoliating agents, sunscreen agents, dyes, pigments, talcum, conditioning agents, hair styling agents, and antidandruff agents.

The consumer product containing microcapsules of the present invention may contain at least one fabric enhancing agent, selected from, but not limited to softening agents, optical brighteners and antistatic agents.

The consumer product contain microcapsules of the present invention may contain at least one preservative selected from, but not limited to butylated hydroxyanisole (BHA), butylated hydroxytoluene (BHT), dilauryl thiodipropionate, alkyl parabene, tocopherols and the like. In another embodiment, a suitable preservative includes a combination of benzisothiazolone (BIT), methylisothiazolone (MIT) and/or laurylamine dipropylenediamine (BDA), and mixtures thereof, and mixtures of N,N'-dihydroxymethyl urea and 1,6-dihydroxy-2,5-dioxo-hexane.

The consumer product containing microcapsules of the present invention may contain at least one deodorizing agent selected from, but not limited to zinc derivatives, essential oils, sodium undecylenate, methyl undecylenate, 2-hydroxypropyl beta cyclodextrin, soyethyl morpholinium ethosulfate, crotonates and fumarates, and alkylene carbonates.

The consumer product containing microcapsules of the present invention may contain least one solubilized, water soluble uncomplexed cyclodextrin selected from, but not limited to alpha-cyclodextrin, beta-cyclodextrin, gamma cyclodextrin and/or their derivatives, and/or mixture thereof.

In another embodiment of the present invention, the consumer product containing the microcapsules of the present invention is a shampoo containing typically from about 3% to 25% by weight, for example from about 12% to about 20% by weight or from about 14% to 18% by weight of one or more anionic surfactants; from about 0.5% to about 20% by weight, for example from about 1% to 10% by weight of zwitterionic and/or amphoteric surfactants; from 0% to about 10% by weight on non-ionic surfactants; from about 20% to about 90% by weight of an aqueous phase, comprising optionally water-soluble solvents; from about 0.0001 to about 0.5% by weight, preferably from about 0.0003 to about 0.1% by weight of one or more preservatives; and optionally benefit agents, such as moisturizers, emollients, thickeners, anti-dandruff agents, hair growth promoting agents, vitamins, nutrients, dyes, hair colorants, and the like.

Further typical formulation ingredients for use in shampoo with our without microcapsules may be found, for example, in EP 0191564 A2 or WO 1997023194 A1.

In one aspect of the invention, a consumer product contains the compositions according to the present invention preferably at a level of about 0.02 to 5 wt %, more particularly from about 0.1 to 2 wt % and still more particularly from about 0.2 to 1 wt % of the shampoo composition.

In another embodiment of the present invention, the consumer product containing the microcapsules of the present invention is a soap bar containing typically from about 20 to about 75 wt %, more particularly from about 35 to about 60 wt % surfactants. Typical surfactants for use in soap bars include but are not limited to anionic surfactants, such as aliphatic sulphonates, such as a primary alkane (e.g., C8-C22) sulphonates, primary alkane (e.g., C8-C22) disulphonates, C8-C22 alkene sulphonates, C8-C22 hydroxyalkane sulphonates or alkyl glyceryl ether sulphonates (AGS); aromatic sulphonates, such as alkyl benzene sulphonate; C12-C18 alkyl sulphate, alkyl ether sulphate, such as alkyl glyceryl ether sulphates; C8-C18 alkyl and C8-C18 alkenyl ether sulphates with more than 1 ethylene oxide unit. The cations include sodium, potassium, ammonium or substituted ammonium.

Ammonium and sodium lauryl ether sulfates are preferred. The anionic may also be alkyl sulfosuccinates (including mono and dialkyl, e.g., C8-C22 sulfosuccinates); alkyl and acyl taurates, alkyl and acyl sarcosinates, sulfoacetates, C8-C22 alkyl phosphates and phosphates, alkyl phosphate esters and alkoxyl alkyl phosphate esters, acyl lactates, C8-C22 monoalkyl succinates and maleates, sulphoacetates, alkyl glucosides and C8-C20 acyl isethionates having general formula $R^1COOC(R^2)HCH_2—(OCH(R^3)CH_2)_xSO_3M$, where $R^1$ is a C8-C20 alkyl moiety, $R^2$ is H or a C1-C4 alkyl moiety, $R^2$ is H or a C1-C4 alkyl moiety, x is an integer having value 0, 1, 2, 3 or 4, and M is the cation; alkyl taurate, having general formula $R^1CONR^2CH_2CH_2SO_3$, where $R^1$ is a C8-C20 alkyl moiety and $R^2$ is a C1-C4 alkyl moiety and M is the cation; and mixtures thereof.

The soap bar typically also contains fatty acid soaps at a level of from about 4 to about 20 wt %, preferably from about 6 to about 12 wt % of the final bar composition. Typical soaps for use in soap contain alkali metal salts of natural of synthetic aliphatic (alkanoic or alkenoic) acids having from about 12 to 22 carbon atoms, preferably from about 12 to about 18 carbon atoms, and mixtures thereof.

The soap bar typically also contains free fatty acids at a level of from about 4 to about 30 wt %, preferably from about 10 to about 25 wt % of the final bar composition. Typical soaps for use in soap include C8-C22 fatty acids, and mixtures thereof.

The soap bar may further contains divalent cation precursors at a level of about 10 to about 12 wt % of the final bar composition. The divalent cation precursors include for example calcium carbonate, magnesium carbonate, calcium chloride and magnesium chloride, and mixtures thereof. The amount of divalent cation precursors must be such that sufficient cation is made available to ensure that most of the soluble soap is bound to the cations so it becomes insoluble. More details about the use of divalent cation precursors may be found in WO 2002012430 A1 which is included here as reference.

The soap bar may further contain amphoteric surfactants comprising C7-C18 alkyl or alkenyl moiety, an acid functional group and a quaternary nitrogen functional group. The level of amphoteric surfactant is typically from about 1 to about 10 wt % of the final bar composition.

Other non-ionic and/or cationic surfactants may also be optionally used at level of from about 0.01 to about 10 wt % of the bar composition.

A comprehensive list of ingredients particularly useful in soap bar may be found in WO 2002012430 A1 which is included here as reference.

In one aspect of the invention, a consumer product contains the compositions according to the present invention preferably at a level of about 0.02 to 5 wt %, more particularly from about 0.1 to 2 wt % and still more particularly from about 0.2 to 1 wt % of the soap bar composition.

In another embodiment of the present invention, the consumer product comprising core-shell microcapsules of the present invention is a liquid soap comprising one or more anionic surfactants, and other surfactants that may be selected from the group consisting of mixtures of fatty acids and neutralized fatty acids, aminoxide surfactants, non-ionic surfactants, zwitterionic surfactants, and mixture thereof; electrolytes; one or more preservatives; and optionally benefit agents that may be selected from the group consisting of pH-control agents, skin care agents, moisturizers, emollients, thickeners, vitamins, nutrients, dyes, and the like.

Typical liquid soap compositions comprise up to 25 wt %, for example from about 8 to about 18 wt % of a fatty acid mixture comprising from about 70 to about 95 wt % of the mixture of C12 and C14 fatty acids and from about 5 to about 30 wt % of the mixture of C16-C20 fatty acid, wherein from about 60 to about 90 mole % of the fatty acids mixture are available in the neutralized form; up to 25 wt % of zwitterionic surfactants, from about 1 to about 25 wt % of anionic surfactant; up to 40 wt % of amine oxide surfactant or mixture thereof having the general formula R1R2R3N→O, such as where R1 and R2 are the same or different and are selected from methyl or ethyl and R3 is a straight chain saturated or unsaturated alkyl group having from about 6-24 carbon atoms.

Further typical formulation ingredients for use in liquid soaps may be found, for example, in CA 2812137 A1 and US 20030050200.

In one aspect of the invention, a consumer product contains the compositions according to the present invention preferably at a level of about 0.02 to 5 wt %, more particularly from about 0.1 to 2 wt % and still more particularly from about 0.2 to 1 wt % of the liquid soap composition.

In another embodiment of the present invention, the consumer product comprising core-shell microcapsules and chitosan of the present invention is a shower gel comprising one or more anionic surfactants, and other surfactants that may be selected from the group consisting of mixtures of fatty acids and neutralized fatty acids, aminoxide surfactants, non-ionic surfactants, zwitterionic surfactants, and mixture thereof; electrolytes, such one or more preservatives; and optionally benefit agents that may be selected from the group consisting of thickeners, pH-control agents; skin care agents, moisturizers, emollients, thickeners, vitamins, nutrients, dyes, and the like.

Typical shower gel compositions comprise from about 3 to about 10 wt % of alkyl ethoxylated sulfate anionic surfactant, up to 10 wt % of amphoteric; up to about 3 wt %, by weight of an N-acylamino acid surfactant, or salt thereof, up to 5 wt % of aminoxide surfactants, up to 2 wt % C8 to C20 fatty alcohol, up to 5 wt % of C14-C22 fatty acid; up to 3 wt % of polymeric thickener that may be selected from the group consisting of cellulose based thickeners such as hydroxypropylmethyl cellulose, sodium carboxymethyl cellulose, hydroxyethyl cellulose, hydrophobically modified HEC, hydroxypropyl cellulose; natural gums and their derivatives xanthan gum, carrageenan gum, gellan gum, guar gum and cationic guars; acrylic cross-polymers, such as carbomers, hydrophobically modified ethoxylated polyurethane and mixture thereof.

Further typical formulation ingredients for use in shower gels may be found, for example, in US 5607678 A and US 20120263668 A1.

In one aspect of the invention, a consumer product contains the compositions according to the present invention preferably at a level of about 0.02 to 5 wt %, more particularly from about 0.1 to 2 wt % and still more particularly from about 0.2 to 1 wt % of the shower gel composition.

Once deposited on the substrate, the core-shell microcapsules are able to release their core material by diffusion through the microcapsule shell or following the mechanical rupture of the microcapsule shell. Mechanical rupture may follow a mechanical action, such as rubbing, squeezing, combing, washing and the like or heating, for example using a hair dryer.

Diffusion-mediated release is particularly desired if the core material is a perfume composition, because, in this case, a nice smell may be perceived over a long time, for example several hours, after application of the microcapsules on the substrate. On the other hand a mechanical rupture may provoke a surprising and pleasant boost of odour.

In order to further illustrate the present invention and the advantages thereof, the following specific examples and comparative example are given, it being understood that same are intended only as illustrative and non-limiting.

EXAMPLES

Example 1: Capsule Synthesis

A series of microcapsules have been prepared according to methods known to the art, using the reagents and emulsifiers shown in Table 1. The polyisocyanates were dissolved in the perfume oil to form an oil phase, which was emulsified in an aqueous phase containing the emulsifier(s), by using a dissolver. The polyamine(s) were added to the emulsion at once or over a pre-defined time, depending on the chosen feed regimen.

For sample A, the method disclosed in WO2007/004166 was used. The aqueous phase was prepared by mixing 1.4 Mowiol 3-96 (polyvinylalcohol, PVA) in 139 g deionized water and heated for 15 min to 60° C. to dissolve the PVA. An oil phase is prepared by dissolving 4.2 g Desmosdur N3300 (ex. Bayer, CAS 28182-81-2), in 60 g perfume. The oil phase was added into the water phase and dispersed using an Ultra Turrax (5 min@11000 rpm). Then, guanidine carbonate (ex. Fluka, CAS 593-85-1) was added to the emulsion which was then heated to 70° C. The emulsion was maintained at this temperature for 10 hours under agitation in order to obtain a slurry of microcapsules.

The data of sample B are those disclosed in US9271905B2, Example 1.

For sample C through F, the method disclosed in EP 2399667 A1, Example 1, was used, with modified levels of polyisocyanates, polyamines and emulsifiers, as reported in Table 1.

In samples D and F, unprotonated chitosan was added at one shot to the slurry once the reaction temperature of 80° C. was reached.

Samples A, B, C and E are comparative examples from the prior art. The microcapsules of samples A and B are based on aromatic polyisocyanates, while those of samples C, D, E and F are based on aliphatic polyisocyanates.

TABLE 1

Reagents and ingredients involved in the synthesis of the microcapsule samples A through F and their level in percentage by weight of the slurry.

| REAGENTS AND INGREDIENTS | A | B | C | D | E | F |
|---|---|---|---|---|---|---|
| POLYISOCYANATE | | | | | | |
| Tris-N-hexamethylene isocyanate-isocyanurate (Desmodur N3330) | 1.5 | | | | | |
| Biuret of hexamethylene diisocyanate (Desmodur N110) | | 2.1 | | | | |
| (Trimethylol propane-adduct of xylylene diisocyanate (Takenate D-110N) | | 1.0 | | | | |
| Dicyclohexylmethane diisocyanate (Desmodur® W) | | | 2 | 1.9 | 3.9 | 3.8 |
| Anionic hexamethylene diisocyanate oligomer (Bayhydur® XP 2547) | | | 0.5 | 0.5 | 1.1 | 1 |
| EMULSIFIER | | | | | | |
| Polyvinylpyrrolidone (PVP K90) | | | 1.5 | 1.5 | 2.5 | 2.5 |
| Polyvinylalcohol (Mowiol 18/4) | | 0.5 | | | | |
| Polyvinylalcohol (Mowiol 3/96) | 0.5 | | | | | |
| Tetraethylammonium chloride | | 0.4 | | | | |
| POLYAMINE | | | | | | |
| Guanidine carbonate | 0.4 | 0.9 | | | | |
| Polyethyleneimine (Lupasol® PR8515) | | | 1.0 | 1.0 | 0.5 | 0.5 |
| Chitosan | | | | 0.1 | | 0.2 |
| Perfume oil | 21.3 | 39.5 | 30 | 30 | 30 | 30 |
| Water | 76.3 | 55.6 | 65 | 65 | 62 | 62 |
| Total | 100 | 100 | 100 | 100 | 100 | 100 |

Example 2: Shampoo Composition

The shampoo composition used in this work is given in Table 2.

TABLE 2

Shampoo composition

| Ingredient trade name | INCI name | Percentage by weight in shampoo |
|---|---|---|
| PROPYLENE GLYCOL | Propylene Glycol | 1.00 |
| JAGUAR C-13S (ex RHODIA) | Guar Hydroxy-propyltrimonium Chloride | 0.25 |
| MARLINAT 242/28 (ex SASOL) | Sodium Laureth Sulfate | 25.00 |
| DEHYTON AB 30 (ex COGNIS) | Coco Betaine | 5.00 |
| EUPERLAN PK 3000 (ex COGNIS) | Glycol distearate, Laureth-4 and Cocoamidopropyl Betaine | 0.50 |
| GLYDANT PLUS LIQ (ex LONZA) | DMDM Hydantoin | 0.50 |
| SODIUM CHLORIDE | Sodium Chloride | 1.20 |
| BC 2102 (ex BALLU CHIMIE) | Dimethiconol Emulsion | 2.00 |
| MICROCAPSULES EX TABLE 1 | | 0.50(*) |
| DEIONIZED WATER | | QSP 100 |

(*)Dry capsules, based on nominal solid content of the slurry

Example 3: Determination of Leakage in Shampoo 0.5 wt % of each of the microcapsules of Table 1 were admixed with the shampoo base of example 2 and stored for one month at 37° C. The perfume having leaked out of the capsules in the base during storage was extracted with cyclohexane and the extract was analyzed by gas chromatography equipped with a flame ionization detector.

TABLE 3

Percentage of the perfume composition that has been leached into the base after one month storage at 37° C., in percentage of the total initial encapsulated perfume composition.

| Sample | 3.1 | 3.2 | 3.3 | 3.4 | 3.5 | 3.6 |
|---|---|---|---|---|---|---|
| Reagents and ingredients according to table 1 | A | B | C | D | E | F |
| Leakage in shampoo base | 90% | 28% | 80% | <20% | >80% | <10% |

As apparent from the results shown in Table 3, incorporating chitosan as part of the thermosetting resin derived from one or more aliphatic polyisocyanates in the shell of core-shell microcapsules confer said microcapsules un-preceding stability with respect to leakage in extractive product bases, such as those prevailing in shampoos. The leakage is even lower than the leakage observed with polyurea microcapsules based on aromatic polyisocyanates known to the art. Furthermore, the results confirm that, using chitosan as part of the thermosetting resin, much less resin may be used in the microcapsule shell, compared to microcapsules known to the art.

Example 4: Olfactive Assessment

The olfactive evaluation was performed on hair swatches. The shampoo samples 3.5 and 3.6 of example 3 were evaluated after 2 weeks storage at 37° C. The shampoo was applied on swatches that have been previously wetted with tap water at a temperature of 37° C. The amount of shampoo was 10% of the weight of the swatches. The shampoo application was performed by gently massaging the swatches during 20 seconds, waiting for 1 minute, rinsing the swatches with tap water at a temperature of 37° C. and removing the excess water by sliding each swatch between two fingers vertically from top to bottom. The olfactive performance was assessed by a panel of four experts on wet stage and after drying for 24 h at room temperature (pre-rub and post-rub), and it was rated on a scale of 1 to 5 (1=barely noticeable, 2=weak, 3=medium, 4=strong and 5=very strong). The results are reported on Table 4.

TABLE 4

Olfactive evaluation scores

| Sample of table 3 | Pre-rub | Post-rub |
|---|---|---|
| 3.5 containg E (comparative example without chitosan) | 0.5 | 0.5 |
| 3.6 containing F (with chitosan) | 2 | 3 |

The invention claimed is:
1. A composition comprising at least one core-shell microcapsule in a suspending medium, wherein said core-shell microcapsule comprises a core containing a functional ingredient and a shell comprising a polyurea resin formed by the reaction of at least one polyisocyanate, chitosan, and at least one other polyamine that is different from chitosan, and/or at least one polyimine within a reaction medium, wherein the chitosan is added to the reaction medium in solid form.

2. The composition of claim 1, wherein the polyurea resin comprise chitosan moieties from 0.1 to 20 wt %, based on the total weight of the polyurea resin.

3. The composition of claim 1, wherein the composition comprise the microcapsules from 10 to 50 wt %, based on the total weight of the composition.

4. The composition of claim 1, wherein the functional ingredient is hydrophobic and the core is in the form of an oil phase.

5. The composition of claim 4, wherein the functional ingredient is a perfume composition, a cosmetic ingredient, or a mixture thereof.

6. The composition of claim 1, wherein the suspending medium is an aqueous phase.

7. The composition of claim 1, wherein the suspending medium is a water-soluble matrix.

8. The composition of claim 1, wherein the polyisocyanate is an aliphatic polyisocyanate.

9. The composition of claim 1, wherein the polyisocyanate is selected from the group consisting of:
- 1,6-diisocyanatohexane,
- 1,5-diisocyanato-2-methylpentane,
- 1,4-diisocyanato-2,3-dimethylbutane,
- 2-ethyl-1,4-diisocyanatobutane,
- 1,5-diisocyanatopentane,
- 1,4-diisocyanatobutane,
- 1,3-diisocyanatopropane,
- 1,10-diisocyanatodecane,
- 1,2-diisocyanatocyclobutane,
- bis(4-isocyanatocyclohexyl)methane,
- 3,3,5-trimethyl-5-isocyanatomethyl-1-isocyanatocyclohexane,
- 2-imidocarbonic diamide,
- biuret,
- aliphatic polyisocyanate based on hexamethylene diisocyanate and alkylene oxide,
- and mixtures thereof.

10. A process of forming the composition of claim 1, comprising the steps of:
  a. forming an oil-in-water emulsion comprising a functional ingredient-containing core oil droplet dispersed in an aqueous phase; and
  b. in the aqeuous phase, reacting at least one polyisocyanate, chitosan, and at least one polyamine that is different from chitosan, and/or at least one polyimine, to form a polyurea core-shell microcapsules in around said droplet to form a core shell microcapsule,
    wherein the chitosan is added in solid form before, during, or after the addition of said at least one polyamine or at least one polyimine.

11. The process of forming the composition of claim 10, wherein chitosan is added in powder form to the reaction medium.

12. A method of increasing the imperviousness of polyurea microcapsule shells, the method comprising the steps of:
  a. forming an oil-in-water emulsion comprising a functional ingredient-containing core oil droplet dispersed in an aqueous phase; and
  b. in the aqeuous phase, reacting at least one polyisocyanate, chitosan, and at least one polyamine that is different from chitosan, and/or at least one polyimine, to form a polyurea core-shell microcapsules in around said droplet to form a core shell microcapsule,
    wherein the chitosan is added in solid form before, during, or after the addition of said at least one polyamine or at least one polyimine.

13. A consumer product selected from the group consisting of:
detergents, cleansing composition, shampoo, conditioner, softener, liquid soap, soap bars, shower gel, deodorant, antiperspirant, or household surface cleaner, wherein the consumer product comprises the composition of claim 1.

14. A method of treating a fabric, skin, hair or a household surface, the method comprising the step of:
applying a consumer product of claim 13 to the fabric, skin, hair or household surface.

15. The composition according to claim 2, wherein the level of chitosan moieties in the polyurea resin is from 0.5 to 10 wt % of moieties derived from chitosan, based on the total weight of the polyurea resin.

16. The composition according to claim 15, wherein the level of chitosan moieties in the polyurea resin is from 0.8 to 5 wt % of moieties derived from chitosan, based on the total weight of the polyurea resin.

17. The composition according to claim 3, wherein the level of microcapsules in the composition is from 25 to 48 wt %, based on the total weight of the composition.

18. The composition according to claim 17, wherein the level of microcapsules in the composition is from 35 to 45 wt % based on the total weight of the composition.

19. The composition according to claim 1, wherein the shell has been formed by a process in which:
the at least one polyisocyanate is first reacted with the at least one other polyamine that is different from chitosan, and/or at least one polyimine within a reaction medium; and,
subsequently the chitosan is added to the reaction medium.

* * * * *